US00PP28187P3

(12) United States Plant Patent
Koppe

(10) Patent No.: US PP28,187 P3
(45) Date of Patent: Jul. 11, 2017

(54) ***BEGONIA* PLANT NAMED 'KRELECE01'**

(50) Latin Name: *Begonia×hiemalis*
Varietal Denomination: KRELECE01

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 42 days.

(21) Appl. No.: 14/756,926

(22) Filed: Oct. 30, 2015

(65) Prior Publication Data

US 2017/0127595 P1 May 4, 2017

(51) Int. Cl.
*A01H 5/02* (2006.01)

(52) U.S. Cl.
USPC ..... Plt./349

(58) Field of Classification Search
USPC ..... Plt./349
See application file for complete search history.

*Primary Examiner* — Keith Robinson
(74) *Attorney, Agent, or Firm* — C. A. Whealy

(57) ABSTRACT

A new and distinct cultivar of *Begonia* plant named 'KRELECE01' characterized by its upright to somewhat outwardly spreading and mounded plant habit; moderately freely branching habit; moderately to freely flowering habit; double flowers that are cerise in color and held above the foliar plane; and excellent postproduction longevity.

2 Drawing Sheets

Botanical designation: *Begonia×hiemalis*.
Cultivar denomination: 'KRELECE01'.

BACKGROUND OF THE INVENTION

The present invention relates to a new and distinct cultivar of *Begonia* plant, botanically known as *Begonia×hiemalis*, commercially referred to as an Elatior *Begonia* and hereinafter referred to by the name 'KRELECE01'.

The new *Begonia* plant is a product of a planned breeding program conducted by the Inventor in De Kwakel and Ermelo, The Netherlands. The objective of the breeding program is to create new vigorous *Begonia* plants with excellent postproduction longevity.

The new *Begonia* plant is a naturally-occurring whole plant mutation of *Begonia×hiemalis* 'Elektra Pink', disclosed in U.S. Plant Pat. No. 18,967. The new *Begonia* plant was discovered and selected by the Inventor as a single flowering plant from within a population of plants of 'Elektra Pink' grown in a controlled greenhouse environment in De Kwakel, The Netherlands in March, 2013.

Asexual reproduction of the new *Begonia* plant by terminal vegetative cuttings taken in a controlled greenhouse environment in Ermelo, The Netherlands since January, 2014 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRELECE01'. These characteristics in combination distinguish 'KRELECE01' as a new and distinct *Begonia* plant:

1. Upright to somewhat outwardly spreading and mounded plant habit.
2. Moderately freely branching habit.
3. Moderately to freely flowering habit.
4. Double flowers that are cerise in color and held above the foliar plane.
5. Excellent postproduction longevity.

Plants of the new *Begonia* differ primarily from plants of the mutation parent, 'Elektra Pink', in flower color as plants of 'Elektra Pink' have pink-colored flowers.

Plants of the new *Begonia* can be compared to plants of *Begonia×hiemalis* 'Dark Netja', not patented. In side-by-side comparisons conducted in Ermelo, The Netherlands, plants of the new *Begonia* differ primarily from plants of 'Dark Netja' in flower color as plants of 'Dark Netja' have light pink-colored flowers. In addition, plants of the new *Begonia* have double flowers whereas plants of 'Dark Netja' have semi-double flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRELECE01' grown in a container.

The photograph on the second sheet are close up views of the upper (right) and lower (left) surfaces of typical leaves and flowers of 'KRELECE01' and in the center of the photograph is a close-up view of typical flower buds with pedicel.

DETAILED BOTANICAL DESCRIPTION

The aforementioned photographs and following observations and measurements describe plants grown during the autumn in 12-cm containers in a shaded glass-covered greenhouse in De Kwakel, The Netherlands and under cultural practices typical of commercial *Begonia* production. During the production of the plants, day and night temperatures averaged 20° C. Plants were ten weeks old when the photographs and description were taken. In the following description, color references are made to The Royal Horticultural Society Colour Chart, 2015 Edition, except where general terms of ordinary dictionary significance are used.

Botanical classification: *Begonia×hiemalis* 'KRELECE01'.

Parentage: Naturally-occurring whole plant mutation of *Begonia×hiemalis* 'Elektra Pink', disclosed in U.S. Plant Pat. No. 18,967.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Upright to somewhat outwardly spreading and mounded plant habit; overall plant shape, broadly oblong.

*Growth habit*.—Moderately vigorous growth habit and moderate growth rate; suitable for 12-cm and larger containers; under optimal environmental and cultural conditions, usually about ten weeks are required to produce proportional plants in 12-cm containers.

*Branching habit*.—Moderately freely branching with about four primary branches each with about four secondary branches.

*Plant height, soil level to top of foliar plane*.—About 22.9 cm.

*Plant height, soil level to top of floral plane*.—About 23.7 cm.

*Plant width*.—About 27.2 cm.

*Lateral branches*.—Length: About 14.8 cm. Diameter: About 1 cm. Internode length: About 2.3 cm. Strength: Moderately strong. Aspect: About 35° from vertical. Texture: Sparsely pubescent. Luster: Glossy. Color: Close to 144A.

*Leaves*.—Arrangement: Alternate, simple. Length: About 12.9 cm. Width: About 9.9 cm. Shape: Ovate. Apex: Acute. Base: Oblique, lobes free. Margin: Crenate. Texture, upper surface: Smooth, glabrous; slightly velvety. Texture, lower surface: Sparse pubescence along veins. Luster, upper and lower surfaces: Slightly glossy. Venation pattern: Laciniate. Color: Developing leaves, upper surface: Close to 147A. Developing leaves, lower surface: Close to 178A. Fully expanded leaves, upper surface: Close to darker than between 147A and N189A; venation, close to 143A. Fully expanded leaves, lower surface: Close to 191A; venation, close to 144A. Petioles: Length: About 4.4 cm. Diameter: About 5 mm. Strength: Low, flexible. Texture, upper and lower surfaces: Sparse pubescence along veins. Luster, upper and lower surfaces: Moderately glossy. Color, upper surface: Close to 152B; distally, close to 183C. Color, lower surface: Close to 146C. Stipules: Length: About 9 mm. Width: About 1 cm. Shape: Broadly ovate. Apex: Obtuse. Base: Broadly cuneate. Margin: Entire. Texture, upper and lower surfaces: Smooth, glabrous. Color, upper surface: Close to 143B; towards the margins, close to 180A. Color, lower surface: Close to 143C; towards the margins, close to 180D.

Flower description:

*Flower appearance and flowering habit*.—Fully double rotate flowers with four tepals and numerous tepaloids; flowers arranged in axillary compound cymes; moderately to freely flowering with typically about nine flowers per cyme and about 100 flowers and flower buds developing per plant; many cymes in flower simultaneously; flowers positioned above the foliar plane and face upright to outwardly.

*Natural flowering season*.—Plants begin flowering about six weeks after planting; plants will flower year round regardless of nyctoperiod, however plants flower earlier and more abundantly from spring into the autumn in The Netherlands.

*Postproduction longevity*.—Individual flowers last about ten days on the plant; flowers not persistent; flowers maintain good substance for about five weeks in an interior environment.

*Fragrance*.—None detected.

*Inflorescence height*.—About 10.9 cm.

*Inflorescence diameter*.—About 9.9 cm.

*Flowers*.—Shape: Rotate, fully double. Diameter: About 5.6 cm. Depth (height): About 2.9 cm.

*Flower buds*.—Length: About 1.3 cm. Diameter: About 0.5 cm to 1.4 cm. Shape: Broadly ovate to nearly circular, flattened. Texture: Glabrous; velvety. Luster: Slightly glossy. Color: Close to 47A.

*Tepals*.—Quantity and arrangement per flower: Usually about four per flower arranged in two whorls. Length: About 3.3 cm. Width: About 4.1 cm. Shape: Reniform. Apex: Rounded. Base: Reniform. Margin: Entire. Texture, upper surface: Smooth, glabrous; moderately velvety. Texture, lower surface: Smooth, glabrous; slightly velvety. Luster, upper and lower surfaces: Matte. Color: When opening, upper surface: Close to 54A; towards the margins, close to 53C. When opening, lower surface: Close to 47C to 47D. Fully opened, upper surface: Close to 54B to 54C; towards the margins, close to 51 A; color does not fade with development. Fully opened, lower surface: Close to 47D; color does not change with development.

*Tepaloids*.—Quantity and arrangement per flower: Usually about 26 per flower arranged in about eight whorls. Length: About 2.1 cm. Width: About 2.1 cm. Shape: Obovate to nearly orbicular. Apex: Rounded. Base: Cuneate. Margin: Entire. Texture, upper surface: Smooth, glabrous; moderately velvety. Texture, lower surface: Smooth, glabrous; slightly velvety. Luster, upper and lower surfaces: Matte. Color: When opening, upper surface: Close to between 53D and 58B. When opening, lower surface: Close to between 54A and 58B. Fully opened, upper surface: Close to 53C to 53D; towards the base, close to 54A to 54B; color does not fade with development. Fully opened, lower surface: Close to 54A to 54B; towards the base, close to 54C; color does not change with development.

*Peduncles*.—Length: About 9.2 cm. Diameter: About 3 mm. Strength: Moderately strong. Aspect: About 30° from lateral branch axis. Texture: Smooth, glabrous. Luster: Moderately glossy. Color: Close to 152B.

*Pedicels*.—Length: About 2.1 cm. Diameter: About 3 mm. Strength: Moderately strong. Aspect: About 30° from lateral branch axis. Texture: Smooth, glabrous. Luster: Glossy. Color: Close to 144B and 152B.

*Flower bracts*.—Quantity per flower: Two. Length: About 1.2 cm. Width: About 1.1 cm. Shape: Ovate. Margin: Entire. Texture, upper and lower surfaces: Smooth, glabrous. Luster, upper and lower surfaces: Matte. Color, upper surface: Close to 143A to 143B; towards the margins, close to 180A. Color, lower surface: Close to 144B; towards the margins, close to 180D.

*Reproductive organs*.—Stamens: None observed. Pistils: None observed.

*Seeds and fruits*.—Seed and fruit production have not been observed as reproductive organs are not formed.

Disease & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRELECE01' as illustrated and described.

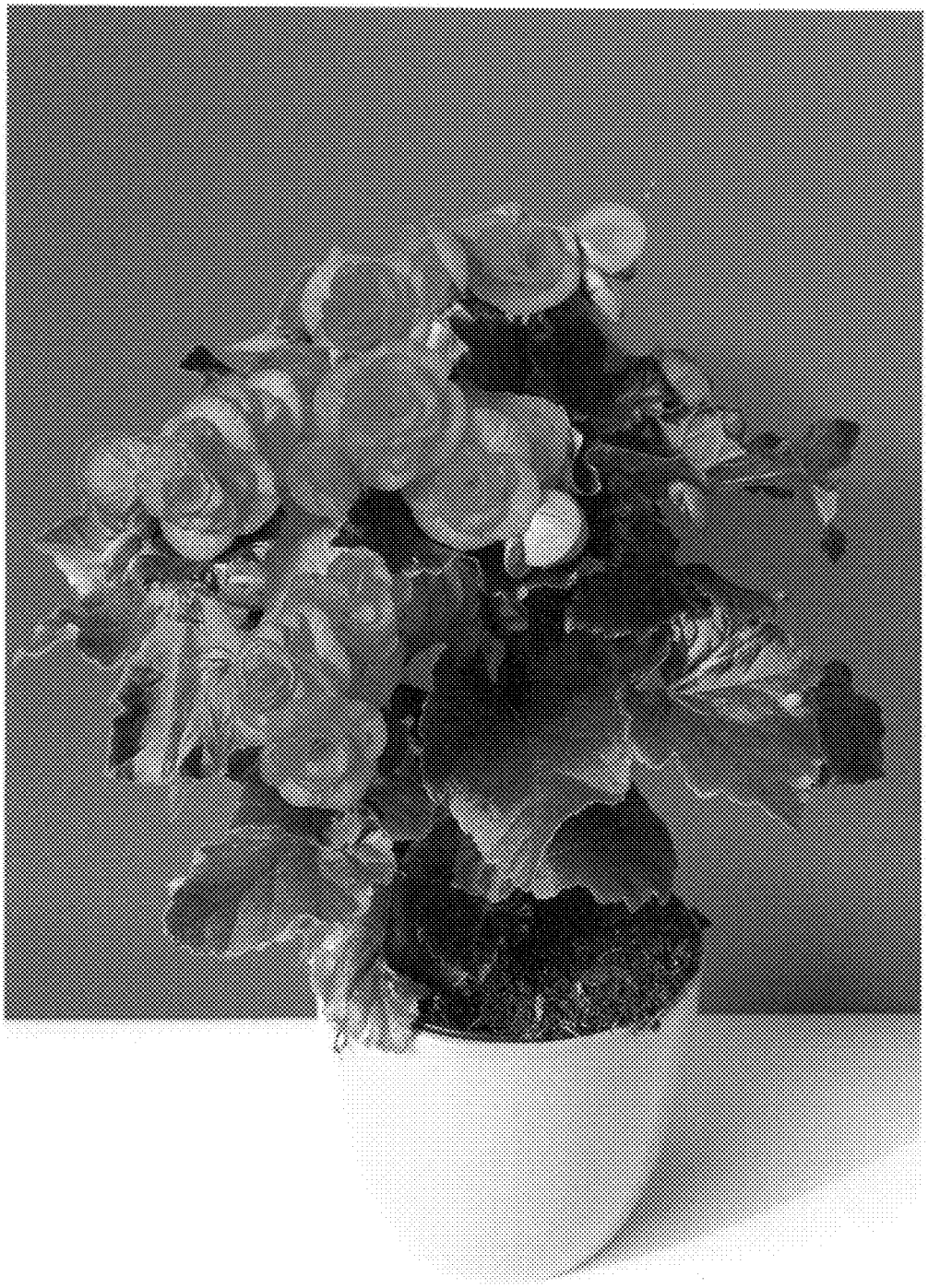

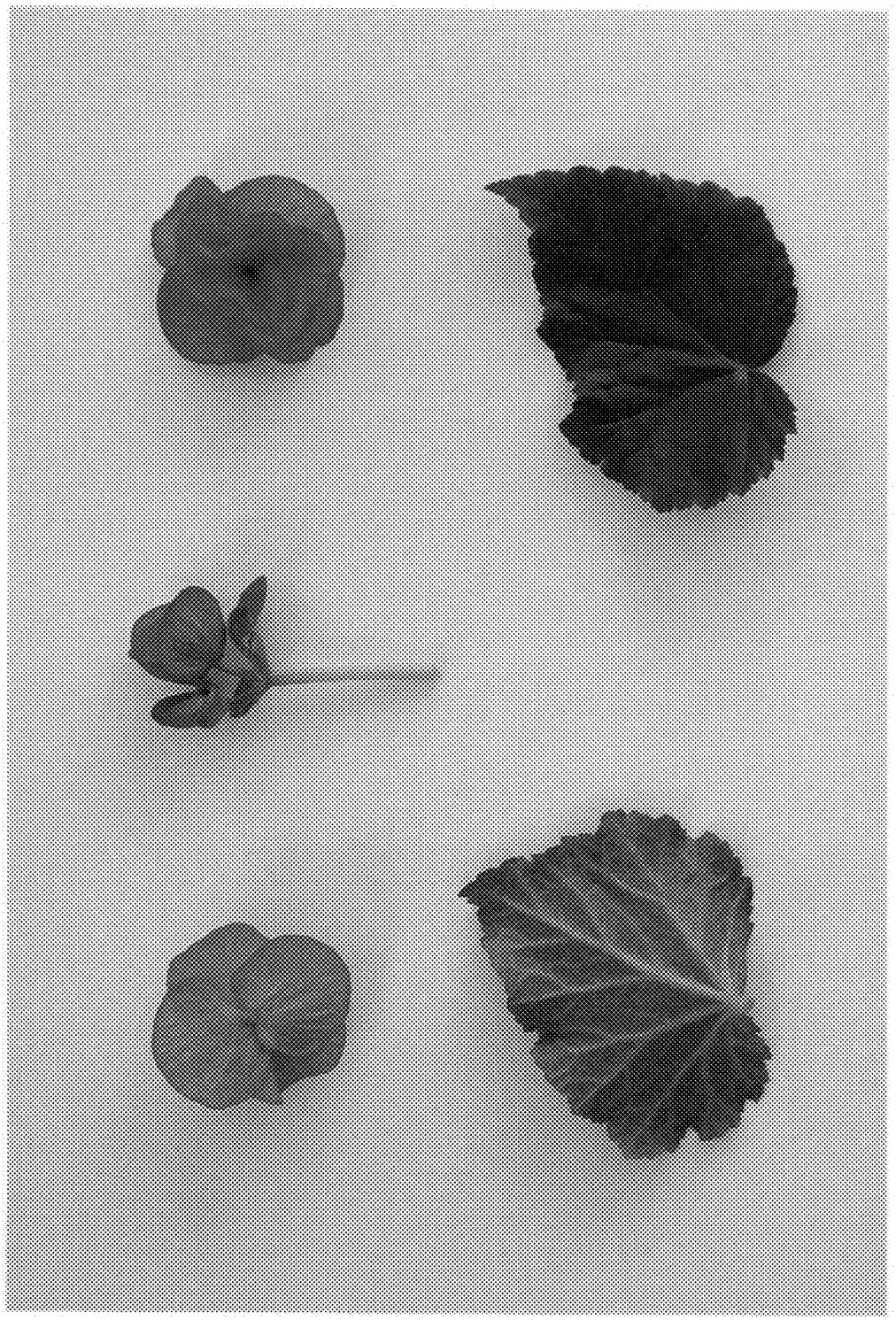

* * * * *